(12) United States Patent
Drewes, Jr.

(10) Patent No.: US 7,879,021 B2
(45) Date of Patent: Feb. 1, 2011

(54) CATHETER WITH NON-UNIFORM WALL THICKNESS

(75) Inventor: David A. Drewes, Jr., Bloomington, IN (US)

(73) Assignee: Sabin Corporation, Bloomington, IN (US)

( * ) Notice: Subject to any disclaimer, the term of this patent is extended or adjusted under 35 U.S.C. 154(b) by 0 days.

(21) Appl. No.: 12/005,192

(22) Filed: Dec. 26, 2007

(65) Prior Publication Data

US 2009/0171318 A1    Jul. 2, 2009

(51) Int. Cl.
*A61M 25/00* (2006.01)
(52) U.S. Cl. .................................... 604/523
(58) Field of Classification Search .......... 604/523–525
See application file for complete search history.

(56) References Cited

U.S. PATENT DOCUMENTS

| 6,855,137 | B2 | 2/2005 | Bon | |
| 2007/0088322 | A1* | 4/2007 | Dicarlo et al. | 604/523 |

* cited by examiner

*Primary Examiner*—Kevin C Sirmons
*Assistant Examiner*—Bradley J Osinski
(74) *Attorney, Agent, or Firm*—Brinks Hofer Gilson & Lione

(57) ABSTRACT

A catheter having a non uniform wall thickness comprising first and second wall regions is described. The first region is thicker than the second region and at least a part of the first region comprises a material having a lower stiffness modulus than the second region. Typically, the ratio of stiffness between the first region and the second region is less than 1.25:1 and preferably approximately 1:1. The first region may comprise the same material as the second region but having a different formulation so that the stiffness modulus is altered. Alternatively, the regions may comprise different materials. The lower modulus material is coextruded into at least a part of the broadest/thicker cross sectional region(s).

15 Claims, 1 Drawing Sheet

CATHETER WITH NON-UNIFORM WALL THICKNESS

FIELD OF THE INVENTION

The present invention relates to a catheter with a non uniform wall thickness.

BACKGROUND OF THE INVENTION

Catheters with a non uniform wall thickness are used in a wide variety of applications such as radiological diagnostics and balloon angioplasty (both cardiac and peripheral procedures). Uneven symmetry in the catheter, caused for example by lumens and/or other structural features which are offset relative to the central axis of the catheter, result in an uneven flexure/flexibility. This is particularly problematic during use of such a catheter when twisting the catheter around a bend in the vessel. Resistance to the twisting motion is encountered by the stiffer portions of the catheter which subsequently whip around the bend when sufficient twisting pressure is applied. This results in a very jerky movement which is undesirable in medical procedures.

SUMMARY OF THE INVENTION

The present invention seeks to provide an improved catheter with a non-uniform wall thickness.

According to a first aspect of the present invention there is provided a catheter having a non-uniform wall thickness comprising first and second wall regions wherein the first wall region is thicker than the second wall region and wherein at least a part of the first wall region comprises a material having a lower stiffness modulus than the second wall region.

In other words, the material in at least a part of the first wall region is more flexible than the material in the second wall region. An advantage of this arrangement is that the stiffness and flexibility of the catheter is evened out in all radial directions. Thus the catheter has a substantially uniform flexibility regardless of the axis in which it is flexed. Accordingly, when the catheter is flexed around a bend in a vessel, there is a reduced and even resistance to twisting and the catheter can be inserted smoothly.

In an embodiment, the ratio of stiffness between the first wall region and the second wall region is less than 1.25:1. Typically, the ratio is approximately 1:1.

The catheter may comprise any suitable material such as nylon, polyamides, flexible PVC, polyolefins, polyurethanes. The first wall region may comprise the same material as the second wall region but having a different formulation so that the stiffness modulus is altered. Alternatively, the wall regions may comprise different materials. The lower modulus material is coextruded into the broadest/thicker cross sectional area(s).

The catheter may be a dual lumen catheter. Dual lumen catheters provide large lumen equivalency whilst maintaining maximum catheter strength.

In one embodiment, the catheter comprises a substantially semi circular lumen spaced apart from a circular lumen, and two wall regions of lower stiffness modulus. The two lumens may be spaced apart in a first axis and the two wall regions of lower stiffness modulus may be spaced apart in a second axis which is perpendicular to the first axis. These wall regions of lower stiffness modulus may be substantially part semi circular in shape.

BRIEF DESCRIPTION OF THE DRAWINGS

Preferred embodiments of the invention will now be described by way of example only and with reference to the drawing in which.

DETAILED DESCRIPTION OF THE INVENTION

Figure 1:
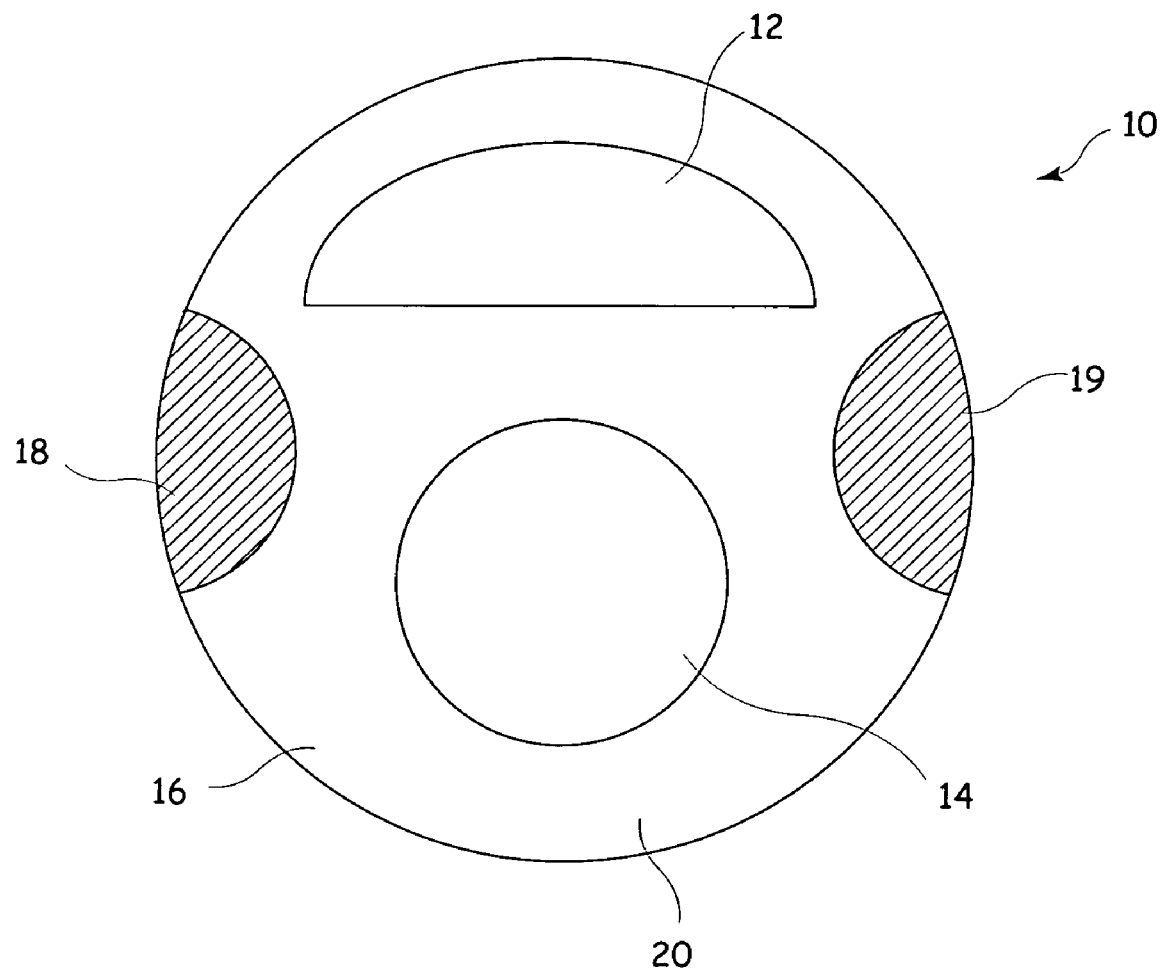
FIG. 1 is a transverse cross section of a dual lumen catheter in accordance with an embodiment of the invention.

Referring to FIG. 1, an embodiment of a catheter 10 having a non-uniform wall thickness has a flattened semi circular lumen 12 which is spaced apart along a first axis from a circular lumen 14. As the lumens are offset relative to the central axis of the catheter and, in this example have different shapes, such a catheter would typically exhibit different flexibilities when biased in different radial directions.

In order to resolve this problem, the catheter 10 has a wall 16 which is provided with two regions 18, 19 which comprise a softer material than the remainder of the catheter material. This reduces the stiffness/increases the flexibility of the catheter in the radial direction of the softer wall regions 18, 19. Since the softer material is located in wall regions 18, 19 which are thicker than other wall regions 20, the catheter has a substantially uniform flexibility in all radial directions. (This is also dependent on the size and shape of the softer regions). The ratio of stiffness between the softer regions and the remainder of the catheter is less than 1.25:1, and is ideally 1:1.

Instead of including softer wall regions, parts of the thicker wall regions could be cut out to address the problem of non uniform flexibility. However, inclusion of the softer regions 18. 19 allows the catheter to retain a circular transverse cross section which has deployment advantages.

In FIG. 1, the softer wall regions 18, 19 which have a lower stiffness modulus (higher flexibility) are approximately semi-circular in cross-section. These areas are co-extruded with the remainder of the catheter 10. Typically, the softer regions comprise the same material as the remainder of the catheter but having a different formulation so that the stiffness modulus is altered. Alternatively, the regions may comprise different materials.

In a specific embodiment, a catheter 10 having a non-uniform wall thickness comprises first 18 and second 20 wall regions wherein the first wall region is thicker than the second wall region. At least a part of the first wall region 18 comprises a material having a lower stiffness modulus than the second wall region 20. The catheter has a third wall region 19 which is also thicker than the second wall region 20. At least a part of the third wall region 19 comprises a material having a lower stiffness modulus than the second wall region 20. The catheter has a first lumen 12 spaced apart from a second lumen 14 in a first axis. The first 18 and third 19 wall regions are spaced apart in a second axis perpendicular to the first axis. The ratio of stiffness between the first (or third) wall region and the second wall region is less than 1.25:1 and typically nearer to 1:1. The catheter comprises any suitable material such as nylon, polyamides, flexible polyvinyl chloride, polyolefines and/or polyurethanes. The first (and/or third) wall region comprises the same material as the second wall region but has a different formulation so that the stiffness modulus is altered.

The catheter may have different luminal configurations (number and/or shape) as long as the cross section is non symmetrical. This may warrant a different number and/or shape of softer wall regions 18, 19. What is important is that at least part of the broadest cross sectional area comprises a material having a lower stiffness modulus.

What is claimed is:

1. A catheter having a plurality of lumens, a circular outer cross-section, and a non uniform wall thickness comprising first and second wall regions wherein the first wall region is thicker than the second wall region, wherein the second wall region consists of a unitary material extending from an outer surface of the catheter to at least one of the plurality of lumens, wherein a first portion of the first wall region comprises a material disposed along an outer surface of the catheter and having a lower stiffness modulus than the unitary material of the second wall region, wherein a remaining portion of the first wall region comprises a material having the same stiffness modulus as the unitary material of the second wall region, and further wherein the catheter has about an uniform flexibility in all radial directions.

2. A catheter as claimed in claim 1 wherein the ratio of stiffness between the first wall region and the second wall region is less than 1.25:1.

3. A catheter as claimed in claim 1 wherein the ratio of stiffness between the first wall region and the second wall region is approximately 1:1.

4. A catheter as claimed in claim 1 comprising at least one compound selected from the following: nylon, polyamides, flexible PVC, polyolefins, and polyurethanes.

5. A catheter as claimed in claim 1 or 4 wherein the first wall region comprises the same material as the second wall region but has a different formulation so that the stiffness modulus is altered.

6. A catheter as claimed in claim 1 wherein the catheter is a dual lumen catheter, comprising a first lumen spaced apart from a second lumen in a first axis.

7. A catheter as claimed in claim 6 wherein the first lumen is a part semi circular lumen and the second lumen is a circular lumen.

8. A catheter as claimed in claim 6 comprising a third wall region which is thicker than the second wall region and wherein at least a part of the third wall region comprises a material disposed along an outer surface of the catheter and having a lower stiffness modulus than the second wall region.

9. A catheter as claimed in claim 8 wherein the wherein the first and third wall regions are spaced apart in a second axis perpendicular to the first axis.

10. A catheter having a circular outer cross-section, and a non uniform wall thickness comprising
first and second wall regions wherein the first wall region is thicker than the second wall region, wherein the second wall region consists of a unitary second material extending from an outer surface of the catheter to at least one of a plurality of lumens, and wherein at least a part of the first wall region comprises a unitary first material disposed along the outer surface of the catheter and having a lower stiffness modulus than the unitary second material of the second wall region,
a third wall region which is thicker than the second wall region, wherein at least a part of the third wall region comprises a unitary third material disposed along the outer surface of the catheter and having a lower stiffness modulus than the unitary material of the second wall region,
a first lumen spaced apart from a second lumen in a first axis, and
wherein the first and third wall regions are spaced apart in a second axis perpendicular to the first axis,
wherein the combined cross-sectional area of the first material and the third material comprise less than ½ of the total cross-sectional area of the catheter, and
wherein the catheter has a substantially equal bending flexibility in all radial directions.

11. A catheter as claimed in claim 1 wherein the unitary material of the second wall region comprises a uniform stiffness modulus.

12. A catheter as claimed in claim 11 wherein the plurality of lumens are each surrounded by the unitary material of the second wall region.

13. A catheter as claimed in claim 10 wherein the unitary second material of the second wall region comprises a uniform stiffness modulus, and wherein the unitary first material and the unitary third material have the same stiffness modulas.

14. A catheter as claimed in claim 13 wherein the first and second lumens are each surrounded by the unitary second material.

15. A catheter comprising an elongate shaft having a circular outer circumference and a plurality of lumens extending at least partially therethrough, the shaft comprising a first region encompassing the plurality of lumens and forming a first portion of the outer circumference of the shaft, and a second region spaced apart from the plurality of lumens and forming a second portion of the outer circumference of the shaft,
wherein the first region consists of a uniform first material having a first stiffness modulus and extending from an outer surface of the catheter to at least one of the plurality of lumens and the second region consists of a uniform second material having a second stiffness modulus, the second stiffness modulus being lower than the first stiffness modulus, and
wherein the shaft has about an uniform flexibility in all radial directions.

* * * * *